US005995632A

United States Patent [19]

Okada

[11] Patent Number: 5,995,632

[45] Date of Patent: Nov. 30, 1999

[54] FAN NOISE CANCELLER

[75] Inventor: Takayuki Okada, Tokyo, Japan

[73] Assignee: NEC Corporation, Tokyo, Japan

[21] Appl. No.: 08/890,621

[22] Filed: Jul. 9, 1997

[30] Foreign Application Priority Data

Jul. 9, 1996 [JP] Japan .................................... 8-179444

[51] Int. Cl.[6] .......................... H03B 29/00; A61F 11/06; F01D 25/04

[52] U.S. Cl. .................... 381/71.3; 381/71.9; 381/71.14; 415/119

[58] Field of Search ........................ 381/71.3, 71.1–71.2, 381/71.4–71.14, 94.1–94.9, FOR 123, FOR 124; 415/119

[56] References Cited

U.S. PATENT DOCUMENTS

| | | | |
|---|---|---|---|
| 4,232,381 | 11/1980 | Rennick et al. | 381/71.9 |
| 5,010,576 | 4/1991 | Hill | 381/71.9 |
| 5,150,855 | 9/1992 | Kaptein | 381/71.4 |
| 5,293,578 | 3/1994 | Nagami et al. | 381/71.14 |
| 5,295,641 | 3/1994 | Kaptein | 381/71.9 |
| 5,423,658 | 6/1995 | Pla et al. | 381/71.2 |
| 5,448,645 | 9/1995 | Guerci | 381/71.14 |
| 5,478,199 | 12/1995 | Gliebe | 381/71.5 |
| 5,511,127 | 4/1996 | Warnaka | 381/71.12 |
| 5,515,444 | 5/1996 | Burdisso et al. | 381/71.5 |
| 5,530,766 | 6/1996 | Hong et al. | 381/71.9 |
| 5,551,649 | 9/1996 | Kaptein | 381/71.4 |
| 5,601,410 | 2/1997 | Quinlan | 415/119 |
| 5,636,287 | 6/1997 | Kubli et al. | 381/71.9 |
| 5,638,454 | 6/1997 | Jones et al. | 381/71.2 |
| 5,692,054 | 11/1997 | Parrella et al. | 381/71.3 |
| 5,692,702 | 12/1997 | Andersson | 381/71.5 |
| 5,791,869 | 8/1998 | Lee | 415/119 |

FOREIGN PATENT DOCUMENTS

| | | |
|---|---|---|
| 0 479 367 A2 | 4/1992 | European Pat. Off. . |
| 0 715 131 A2 | 6/1996 | European Pat. Off. . |
| 62-1156 | 1/1987 | Japan . |
| 63-284999 | 11/1988 | Japan . |
| 1128000 | 8/1989 | Japan . |
| 3-231599 | 10/1991 | Japan . |
| 3294731 | 12/1991 | Japan . |

OTHER PUBLICATIONS

G.H. Koopmann et al., "Active Source Cancellation of the Blade Tone Fundamental and Harmonics in Centrifugal Fans," *Journal of Sound and Vibration* (1988) vol. 126, Oct. 22, 1988, pp. 209–220.

*Primary Examiner*—Forester W. Isen
*Assistant Examiner*—Xu Mei
*Attorney, Agent, or Firm*—Sughrue, Mion, Zinn, Macpeak & Seas, PLLC

[57] ABSTRACT

A fan noise canceller includes a rotation information detecting device for detecting noise information of a fan, a band-pass filter for extracting the blade passing frequency from the noise information, an output control device for controlling the amplitude and phase of the blade passing frequency signal of the extracted noise information, and a cancelling loud-speaker for converting the output of the output control device into a sound signal.

5 Claims, 8 Drawing Sheets

FAN NOISE CANCELLER

BACKGROUND OF THE INVENTION

The present invention relates to fan noise cancellers and, more particularly, to a fan noise canceller, which is applicable to all fans, such as cooling fans for home electric products and office appliances and also air conditioner fans, and adopts an active system.

Fan noise muffling techniques are roughly classified into those of a passive system, which use sound absorbers and sound insulators, and those of an active system, which positively generate a sound wave in the opposite waveform relation to the fan noise and muffle the fan noise by sound wave interference.

A conventional active noise cancellation system for fans is shown in FIG. 8.

As shown, this fan noise canceller comprises a first microphone 51 disposed in a duct 100 at a position near a fan 50, a second microphones 52 disposed in the duct 100 and at a predetermined distance from the first microphone 51, and a muffling loud-speaker 53 disposed mid way between the microphones 51 and 52.

The fan noise canceller further comprises a controller 54 for controlling the sound wave for cancelling the fan noise outputted from the cancelling loud-speaker 53 according to input signals from the first and second microphones 51 and 52.

In this fan noise canceller, a sound wave which is generated from the fan 50 and propagated through the duct 100 is detected by the first microphone 51 and coupled to the controller 54. At this time, a signal from the second microphone 52 which evaluates the cancelling effect is also coupled to the controller 54.

The second microphone 52 for evaluating the cancelling effect, detects a sound wave that results from the interference of the sound wave generated from the cancelling loud-speaker 53 and the sound wave propagated from the fan 50. The controller 54 drives the cancelling loud-speaker 53 by generating, in a digital signal processing or like process, a signal for canceling the signal from the second microphone 52. This has an effect of reducing noise at the position, at which the second microphone 52 is disposed.

The conventional fan noise canceller as shown above has an advantage that it can be installed after the installation of the fan 50. It also has an advantage that it cancels noise on the side of the second microphone 52 (i.e., adjacent the duct end from which air is sent out), and the operation thus is not readily affected by the noise characteristic changes or system changes over time.

In the above conventional fan noise canceller, however, the first microphone 51 and the cancelling loud-speaker 53 are disposed to form a closed loop as an electrical-acoustical system. Therefore, the operation of the controller 54 readily becomes unstable, and sometimes howling occurs to increase the noise.

In addition, in the conventional fan noise canceller a harmonic wave is generated by detecting the number of rotations of the fan. Therefore, a predetermined time is required for the signal processing that is necessary for generating the opposite waveform sound wave. For this reason, this fan noise canceller is unsuitable for a fan which does not have a duct. Therefore, in the conventional fan noise canceller it is necessary to provide a duct or the like.

SUMMARY OF THE INVENTION

An object of the present invention is to overcome the disadvantages of the conventional fan noise canceller and effectively reduce at least the level of the high noise level blade passing frequency, thus providing an efficient and highly reliable fan noise canceller.

According to a first aspect of the present invention, there is provided a fan noise canceller comprising rotation information detecting means for detecting fan rotation information containing the blade passing frequency of noise generated from a fan with the rotation thereof and converting the detected information into an electric signal, a frequency component extracting means for receiving the output of the rotation information detecting means and extracting the blade passing frequency of the noise generated from the fan, an output control means for controlling the amplitude and phase of a blade passing frequency signal of the noise extracted by the frequency component extracting means, and a cancelling loud-speaker for converting an electric signal covering the blade passing frequency signal outputted from the output control means into a sound signal and providing sound of the sound signal for propagation in an interfering relation to noise from the fan, wherein the rotation information detecting means includes a rotatable disc coupled to the shaft of the fan and carrying change information corresponding to the number of blades of the fan, and a signal detector for detecting rotation information of the rotatable disc and outputting signals of the blade passing frequency contained in the rotation information and equal to the product of the number of rotations of the fan and the number of blades thereof and harmonics of the blade passing frequency as electric signals.

In the first aspect of the present invention, the rotation information detecting means which is operable with the rotation of the fan, generates an electric signal containing a frequency equal to the product of the "number of rotations per second" and the "number of blades", and on the basis of this electric signal, reference signals for cancelling feature frequency noises of the fan are generated.

Among the reference signals thus generated, a feature frequency signal (here a blade passing frequency signal) is extracted by the frequency component extracting means, which extracts the frequency equal to the product of the "number of rotations per second" and the "number of blades". The extracted signal and the linear feature frequency noise are strongly correlated to each other, and the output control means for changing the amplitude and phase of the extracted signal, generates an opposite waveform to the linear feature frequency noise. Finally, the loud-speaker generates the opposite waveform sound wave, which is propagated in an inferring relation to the fan noise, thus realizing the cancelling.

The fan noise frequency comprises a wideband component resulting from eddy, separation, etc., and discrete noise components which are attributable to the rotation (i.e., pronounced peak components appearing at harmonics of the rotation frequency). Of the latter components, the one at the frequency equal to the product of the "number of rotations per second" and the "number of blades" of the fan is extremely pronounced. Cancelling this component thus contributes significantly to the reduction of the fan noise.

According to a second aspect of the present invention, there is provided a fan noise canceller comprising rotation information detecting means for detecting fan rotation information containing the blade passing frequency of noise generated from a fan with the rotation thereof and converting the detected information into an electric signal, a frequency component extracting means for receiving the output of the rotation information detecting means and extracting the blade passing frequency of the noise generated from the fan, an output control means for controlling the amplitude and phase of a blade passing frequency signal of the noise extracted by the frequency component extracting means, and a cancelling loud-speaker for converting an electric signal covering the blade passing frequency signal outputted from the output control means into a sound signal and providing sound of the sound signal for propagation in an interfering relation to noise from the fan, wherein the rotation information detecting means includes magnetic members respectively installed on each respectively of the fan blades, a magnetic sensor disposed in the vicinity of the fan facing the magnetic members, and a pre-amplifier for amplifying the output of the magnetic sensor and outputting the amplified output to the frequency component extracting means.

In the second aspect of the present invention, in addition to obtaining the functions obtainable according to the first aspect of the present invention, the rotation information detecting means includes the magnetic members and the magnetic sensor disposed in the vicinity of the fan and facing the magnetic members, reducing the size of the rotation information detecting means.

According to a third aspect of the present invention, there is provided a fan noise canceller comprising rotation information detecting means for detecting fan rotation information including the blade passing frequency of noise generated from a fan with the rotation thereof, a plurality of frequency component extracting means operable according to the fan rotation information detected by the rotation information detecting means to independently detect the blade passing frequency and one or more harmonics thereof of the fan noise, a plurality of output control means for independently controlling the level and phase of the blade passing frequency and one or more harmonic components outputted from the frequency component extracting means, a cancelling loud-speaker for converting signals outputted from the output control means into sound signals and providing the sound of these sound signals for propagation in an interfering relation to noise from the fan, and an output synthesizer provided between the plurality of output control means and the cancelling loud-speaker for combining the outputs of the output control means.

In the third aspect of the present invention, in addition to achieving the functions of the second aspect of the present invention, a plurality of amplitude and phase control means are provided for the blade passing frequency and also for harmonics thereof. It is thus possible to muffle the blade passing frequency with or without simultaneous cancelling of feature frequency components of desired degrees.

Also, with the provision of means for adding together the signals of the amplitude and phase control means, the amplitude and phase control in each channel may be executed independently without affecting or being affected by the amplitude and phase control stage of the other channels. By reducing the plurality of pronounced peak components it is possible to more effectively muffle the fan noise.

According to a fourth aspect of the present invention, there is provided a fan noise canceller which further comprises a noise level detecting means disposed in a fan noise propagation space for monitoring the fan noise cancelling status, and a controller for controlling the amplitude and phase of frequencies concerning the fan noise by controlling at least the output control means according to the noise level detected by the noise level detecting means, thereby setting an optimum cancelling state.

In the fourth aspect of the present invention, the noise level detecting means (i.e., microphone) disposed in the fan noise propagation space monitors the effect of cancelling by sound wave interference, i.e., the system operation status, and information indicating the cancelling effect is simultaneously inputted to the controller. The controller thus can set the amplitude and phase to optimum values to reduce the noise to optimum levels by the sound wave interference.

According to the first to fourth aspects of the present invention, the reference signals are obtained directly from the fan rotation. It is thus possible to eliminate hauling and extremely reduce the waveform processing time. Thus, the opposite waveform sound wave generation means can be disposed in the vicinity of the noise source, thus permitting system size reduction and realization of a cancelling system, which can follow fan rotation variations and is highly reliable.

More specifically, the present invention provides a fan noise canceller comprising: a rotation information detecting means for detecting noise information of a fan; a band-pass filter for extracting the blade passing frequency signal from the noise information; an output control means for controlling the amplitude and phase of the blade passing frequency signal of the extracted noise information; and a cancelling loud-speaker for converting the output of the output control means into a sound signal, wherein the rotation information detecting mean includes a rotatable disc coupled to a shaft of the fan and carrying change information corresponding to the number of fan blades, and a photo-interrupter for outputting signals of the blade passing frequency and harmonics thereof contained in the rotation information of the rotatable disc as electric signals.

The present invention also provides a fan noise canceller comprising: rotation information detecting means for detecting rotation information of a fan including a blade passing frequency of noise generated with the rotation of the fan and converting the detected information into an electric signal; a plurality of band-pass filters as frequency component extracting means operable according to the fan rotation information detected by the rotation information detecting means for independently extracting the blade passing frequency and one or more harmonic components of the fan noise; a plurality of output control means for independently controlling the output level and phase of the blade passing frequency and one or more harmonic components extracted by the band-pass filters; and a cancelling loud-speaker for converting signals outputted from the output control means into sound signals and providing the sound thereof for propagation in an interfering relation to the noise propagated from the fan; wherein an adder for combining the outputs of the output control means is provided between the output control means and the cancelling loud-speaker and the output control means includes a phase controller for setting the opposite phase to the phase of the input electric signal, and a level controller for setting a predetermined level of the negative polarity to the signal level of the electric signal, the output control means control the phase and level of the blade passing frequency equal to the number of rotations per second and the number of blades and harmonics of the blade passing frequency to provide the opposite phase blade passing frequency and harmonics thereof, which are added together in the adder as the output synthesizer, and the output of the adder is coupled to the cancelling loud-speaker, which thus provides a sound wave in the opposite waveform relation to each feature frequency of the fan noise.

Other objects and features will be clarified from the following description with reference to attached drawings.

BRIEF DESCRIPTION OF THE DRAWINGS

FIG. 6(A) shows the spectrum of the noise of the fan 11 without being muffled;

PREFERRED EMBODIMENTS OF THE INVENTION

Now, embodiments of the present invention will be described with reference to the drawings.

Figure 1:
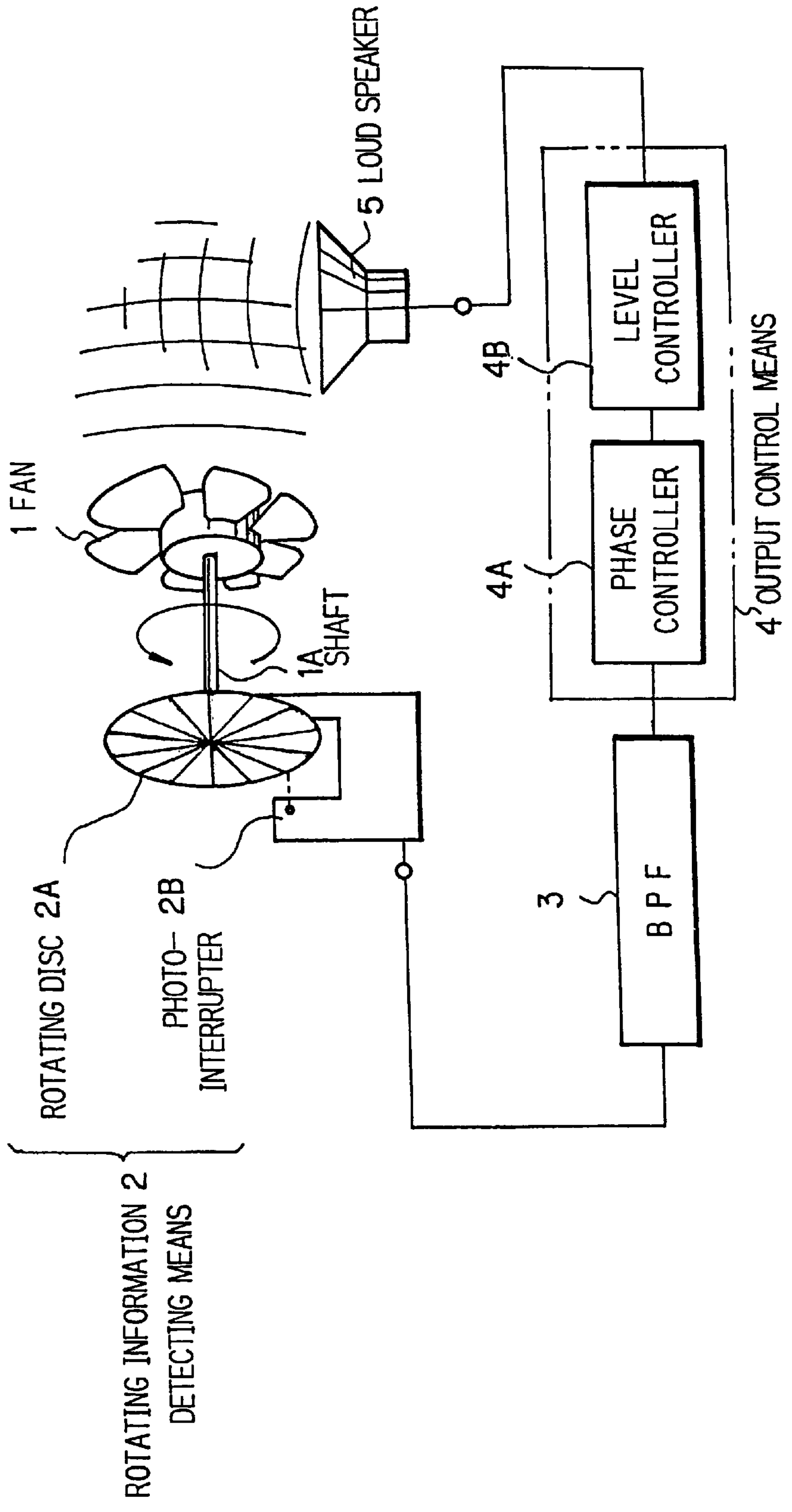
FIG. 1 shows a first embodiment of the present invention.

FIG. 1 shows a first embodiment of the present invention. Referring to FIG. 1, reference numeral 1 designates a seven-blade fan. The fan 1 has a shaft 1A, on which a rotation information detecting means 2 is provided. The rotation information detecting means 2, as will be described later, detects rotation information of the fan 1 including the blade passing frequency of noise generated with the rotation of the fan 1 and converts the detected information into an electric signal.

The first embodiment shown in FIG. 1 further comprises a band-pass filter 3 as a frequency component extracting means for receiving the output of the rotation information detecting means 2 and extracting the blade passing frequency of the noise generated from the fan 1, an output control means 4 or controlling the amplitude and phase of a blade passing frequency wave signal of the noise extracted by the frequency component extracting mean. (i.e., band-pass filter 3), and a cancelling loudspeaker 5 for converting an electric signal obtained from the blade passing frequency signal, outputted from the output control means 4, into a sound signal and providing the sound of this signal in an interfering relation to the noise generated and propagated from the fan 1.

The output control means 4 includes a phase controller 4A for setting the opposite phase to the phase of the electric signal obtained from the blade passing frequency signal, and a level controller 4B for setting a level which is of the opposite polarity (i.e., negative) with respect to the level of the electric signal obtained from the blade passing frequency signal (that is, a level suitable for cancellation).

The rotation information detecting means 2 includes a rotating disc 2A, which is coupled to the shaft 1A of the fan 1 and has radially uniformly and alternately arranged light-transmitting and light-blocking areas, and a signal detector 2B for detecting rotation information of the rotating disc 2A. The rotating disc 2A specifically has a total of fourteen radially uniformly and alternately arranged light-transmitting and light-blocking areas in conformity to the seven blades of the fan 1, and the signal detector 2B is a photo-interrupter.

The rotating disc 2A is rotated in a timed relation to the fan 1 to transmit and block the light from the signal detector (or photo-interrupter) 2B. With this operation, the signal detector 2A provides a signal, the main component of which is at a frequency equal to the product of the number of rotations per second and the number of blades, i.e. the "blade passing frequency".

The band-pass filter 3 extracts only the frequency equal to the product of the number of rotations per second and the number of blades (i.e., the blade passing frequency) of the output signal from the signal detector 2B. The blade passing frequency is equal to the linear feature frequency of the fan noise.

The phase and level controllers 4A and 4B control the phase and amplitude, respectively, of the fan noise signal at the blade passing frequency that is extracted from the band-pass filter 3, thus providing a sound wave, which is in the opposite waveform relation (i.e., with a waveform 180 degrees out-of-phase with respect to the waveform of) the first-order feature frequency (blade passing frequency) of the fan noise, generated from the cancelling loud-speaker 5.

Consequently, the first-order feature frequency noise is muffled by the sound wave interference to provide effective noise reduction.

In the first embodiment, the noise cancelling is made with respect to the sole blade passing frequency signal of the fan noise. However, it is also possible to construct various parts of the fan noise canceller for fan noise reduction with respect to particular harmonics that are harsh to the ears, such as the first or third harmonic.

Figure 2:
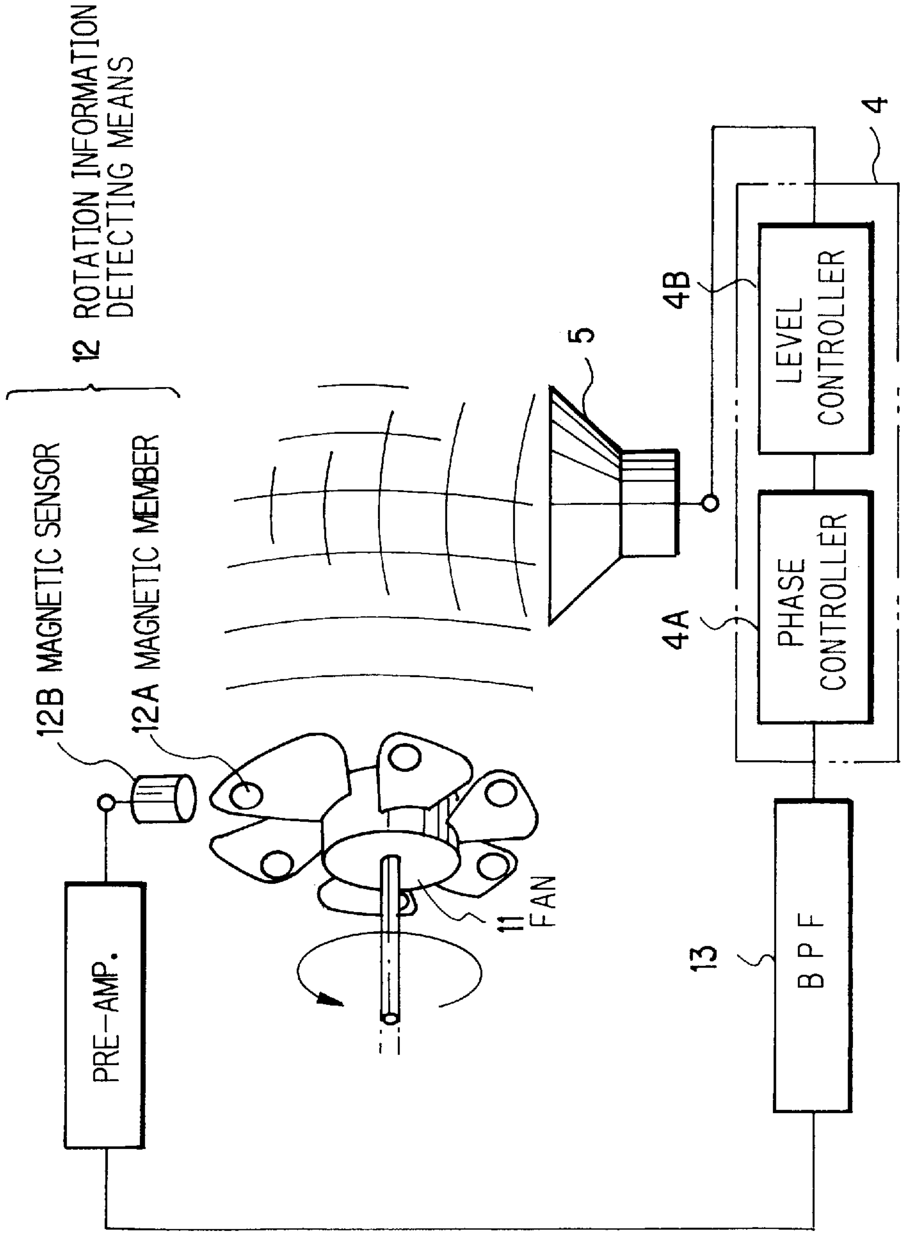
FIG. 2 shows a second embodiment of the present invention.

FIG. 2 shows a second embodiment of the present invention. In FIG. 2, reference numeral 11 designates a six-blade fan. Along the edge of the zone of rotation of the fan 11, a rotation information detecting means 12 is disposed such that it faces the fan 11. The rotation information detecting means 12 detects fan rotation information including the blade passing frequency of noise generated with the rotation of the fan 11 and converts the detected information into an electric signal.

The rotation information detecting means 12 includes magnetic members 12A respectively provided on each blade of the fan 11, a magnetic sensor 12B disposed in the vicinity of the fan 11 to be capable of facing each magnetic member 12A, and a pre-amplifier 12C for amplifying the output of the magnetic sensor 12B and providing the amplified output to a frequency component extracting means (i.e., a band-pass filter) 13.

Other elements of this embodiment are the same as the first embodiment shown in FIG. 1.

In the second embodiment shown in FIG. 2, a reference signal can be obtained by the combination of the magnetic sensor 12B and the magnetic members 12A provided on each blade of the fan 1.

Magnetic field changes caused as each magnetic member 12A passes by the magnetic sensor 12B are detected by the magnetic sensor 12B. The magnetic members 12A are respectively provided on each blade of the fan 11 in order to obtain a harmonic of the blade passing frequency, which is equal to the product of the number of rotations per second and the number of blades.

A detection signal from the magnetic sensor 12B is coupled to a band-pass filter 13, which selectively passes a feature frequency of a desired degree, which cancelling is to be executed with respect to. Like the first embodiment, the phase and amplitude of the output signal of the band-pass filter 13 are controlled for cancelling the feature frequency noise of the desired degree. The fan noise thus can be effectively reduced.

In the second embodiment, the cancelling is executed with respect to the sole blade passing frequency wave of the fan noise. However, it is also possible to construct various parts of the fan noise canceller for fan noise reduction with respect to a harmonic that is harsh to the ears, such as the first or third harmonic.

Figure 3:
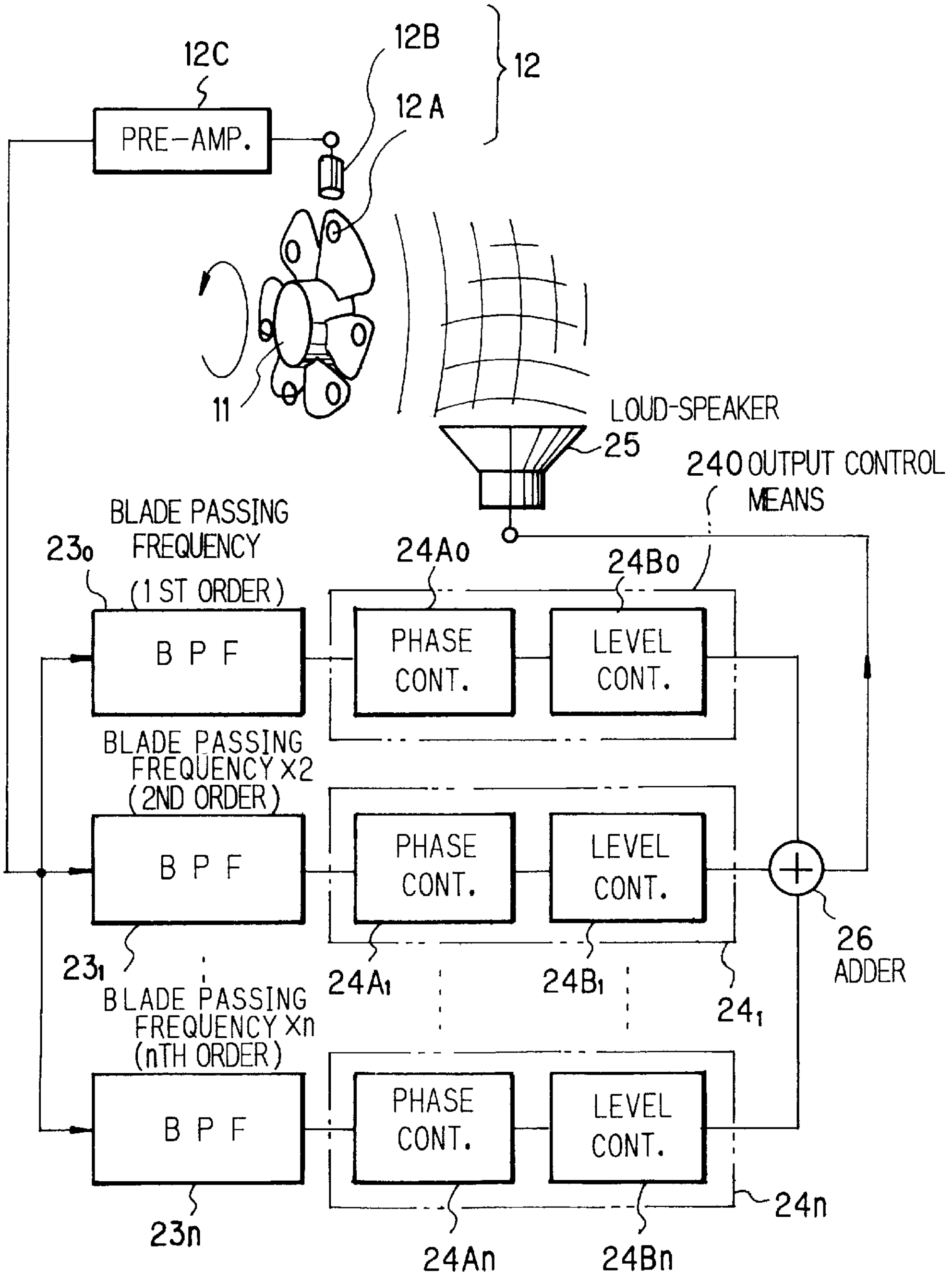
FIG. 3 shows a third embodiment of the present invention.

FIG. 3 shows a third embodiment of the present invention. Elements similar to those of FIG. 2 are designated by like reference numerals and symbols.

As shown in the figure, this embodiment comprises rotation information detecting means 12 for detecting the rotation information of a fan 11 including the blade passing frequency of noise generated with the rotation of the fan 11 and converting the detected information into an electric signal, a plurality of band-pass filters $23_0$, $23_1$ to $23_n$ as frequency component extracting means operable according to the fan rotation information detected by the rotation information detecting means 12 for independently extracting the blade passing frequency and one or more harmonic components of the fan noise, a plurality of output control means $24_0$ to $24_n$ for independently controlling the output level and phase of the blade passing frequency and one or more harmonic components extracted by the band-pass filters $23_0$ to $23_n$, and a cancelling loud-speaker 25 for converting signals outputted from the output control means $24_0$ to $24_n$ into sound signals and providing the sound thereof for propagation in an interfering relation to the noise propagated from the fan 11.

An adder 26, which is a synthesizer for combining the outputs of the output control means $24_0$ to $24_n$, is provided between the output control means $24_0$ to $24_n$ and the cancelling loud-speaker 25.

The output control means $24_0$ includes a phase controller $24A_0$ for setting the opposite phase to the phase of the input electric signal, and a level controller $24B_0$ for setting a predetermined level of the opposite polarity of the signal level of the electric signal (i.e., an optimum level for the cancelling).

The other output control means $24_1$ to $24_n$ are constructed likewise, including phase controllers $24A_1$ to $24A_n$ and level controllers $24B_1$ to $24B_n$.

Similar to the embodiment of FIG. 1, the output control means $24_0$ to $24_n$ control the phase and level of the blade passing frequency equal to the product of the number of rotations per second and the number of blades and harmonics of the blade passing frequency to provide the opposite phase blade passing frequency and harmonics thereof, which are added together in the adder 26 as the output synthesizer. Similar to the embodiment of FIG. 1, the output of the adder 26 is coupled to the cancelling loud-speaker 25, which thus provides a sound wave in the opposite waveform relation to each feature frequency of the fan noise.

The feature frequency noise is thus muffled by the sound wave interference to achieve effective noise reduction.

The construction as shown may be arranged to operate either one or some of the band-pass filters $23_0$ to $23_n$. This arrangement permits cancelling feature frequency sounds with respect to the blade passing frequency and particular one or ones of harmonics coupled to the pertinent band-pass filters.

The individual channel signals described above are combined in the adder 26, and the resultant signal, obtained from the independently phase and level controlled channel components, drives the loud-speaker 25 for the fan noise reduction.

Figure 4:
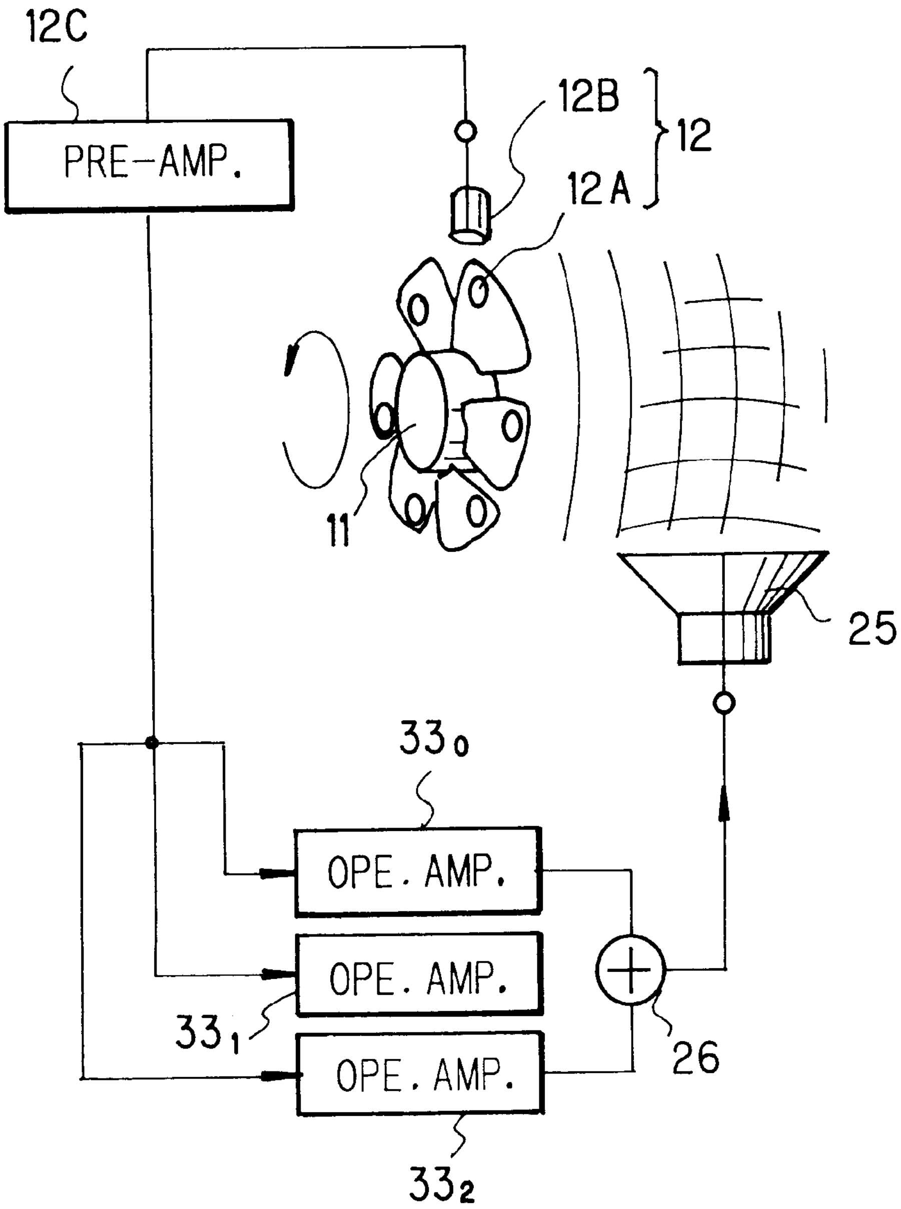
FIG. 4 shows a fourth embodiment of the present invention.

FIG. 4 shows a fourth embodiment of the present invention. Parts like those shown in FIG. 3 are designated by like reference numerals and symbols.

Figure 5A:
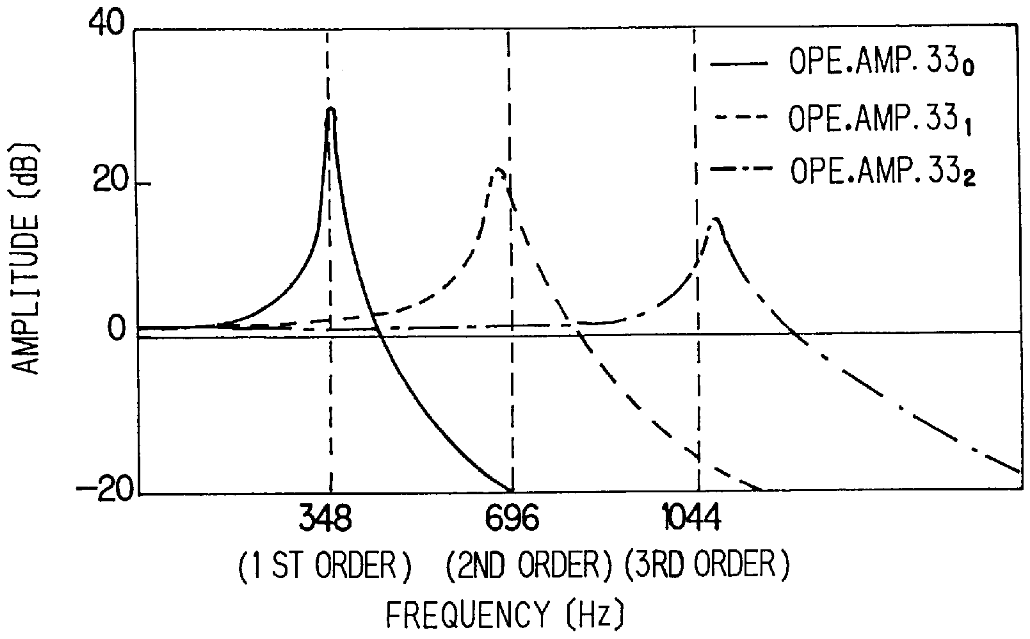
FIGS. 5(A) and 5(B) show the frequency characteristics of the operational amplifiers $\mathbf{33}_0$ to $\mathbf{33}_n$ in FIG. 4.
Figure 5B:
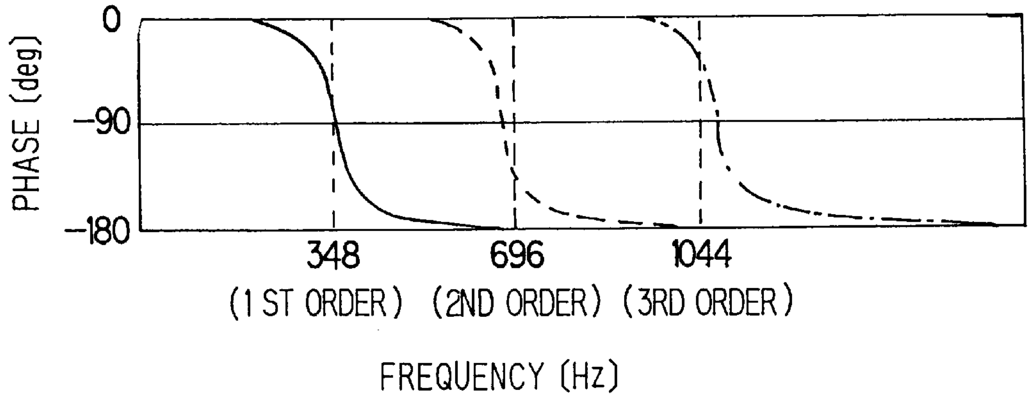

The fourth embodiment comprises a plurality of operational amplifiers $33_0$ to $33_n$, which are provided in lieu of the band-pass filters $23_0$ to $23_n$ and the output control means $24_0$ to $24_n$ of the third embodiment shown in FIG. 3, the output control means $24_0$ to $24_n$ controlling the phase and level of the blade passing frequency and one or more harmonics outputted from the band-pass filters $23_0$ to $23_n$. FIG. 5 shows the frequency characteristics of the operational amplifiers $33_0$ to $33_n$. Elements other than the operational amplifiers $33_0$ to $33_n$ are the same as in the previous embodiment shown in FIG. 3.

The fourth embodiment shown in FIG. 4 seeks cancelling the first to third harmonics of the feature frequency of the fan noise.

It has been experimentally confirmed that with respect to the first to third harmonics of the feature frequency noise, the phase lag of the fan noise feature frequency and feature frequency components obtained from reference signals is 70°, 140° and 35°, respectively, and the amplification degree necessary for the sound wave generated from the loud-speaker 25 is 30, 20 and 10 Db, respectively.

It is thus possible to replace the band-pass filters $23_0$ to $23_2$ and the output control means $24_0$ to $24_2$ shown in FIG. 3 with appropriate selection of the resonant frequency and the Q value of operational amplifiers for obtaining the desired amplification degree and phase lag.

In the fourth embodiment, for the operational amplifiers $33_0$ to $33_2$, the amplification degree is set to 30, 20 and 10 Db, respectively, and the phase lag is set to 70°, 140° and 35°, respectively.

The output signals of the operational amplifiers $30_0$ to $30_2$ are combined in the adder 26, the output of which in turn drives the loud-speaker 25, thus realizing the cancelling of the first to third harmonics of the feature frequency.

Figure 6A:
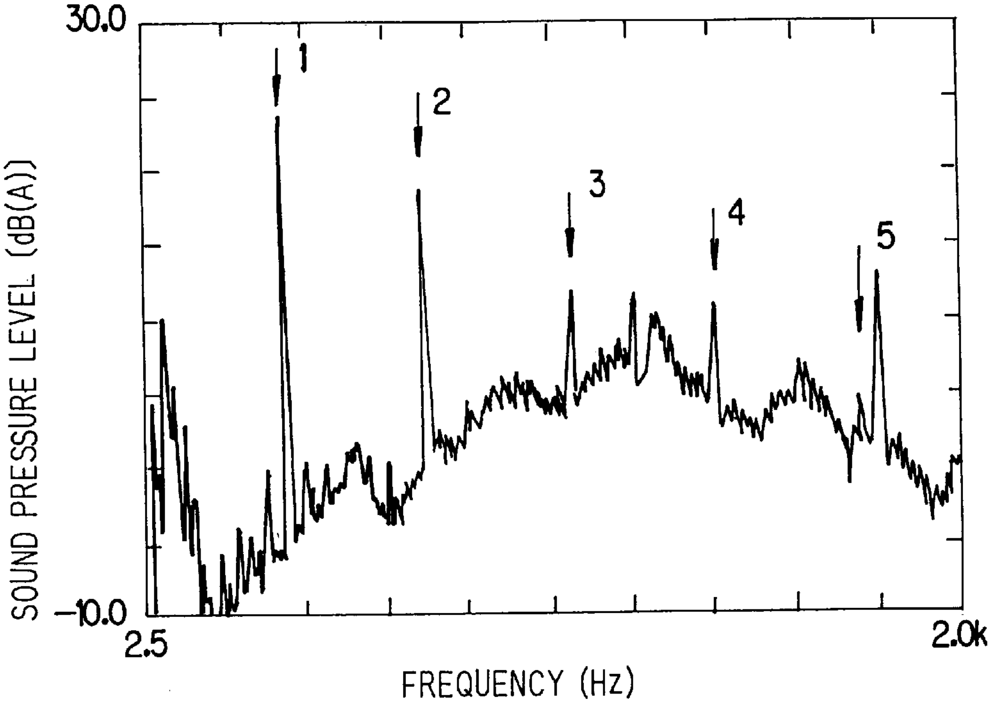
FIGS. 6(A) and 6(B) show experimental results.
Figure 6B:
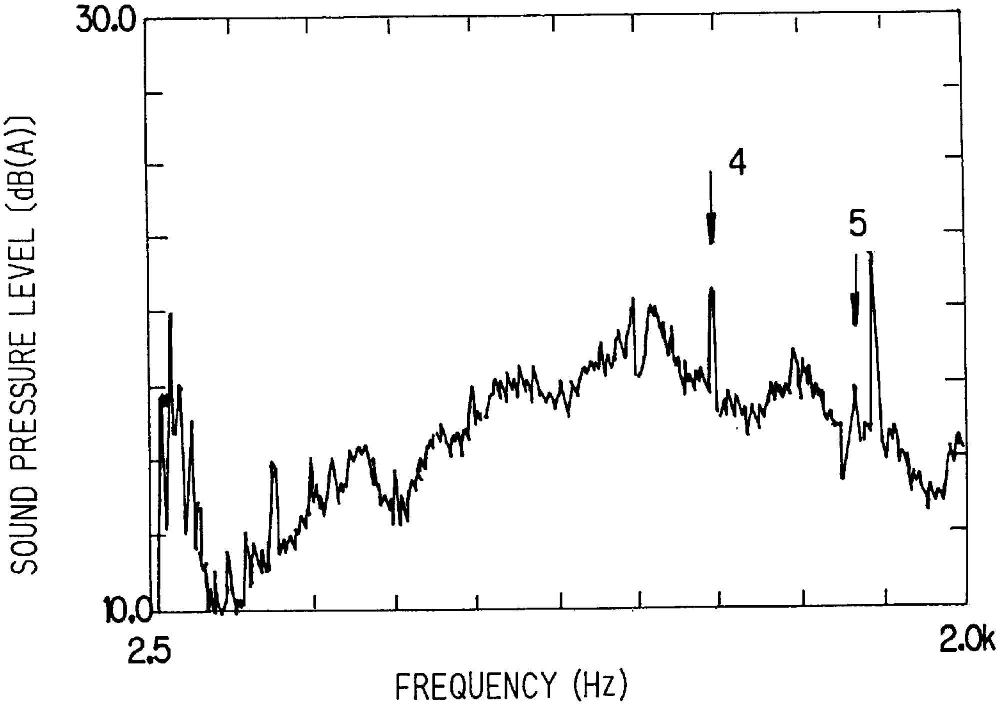

FIGS. 6(A) and 6(B) show experimental results. FIG. 6(A) shows the spectrum of the noise of the fan 11 without being muffled. This spectrum has pronounced peaks as the first to third harmonics of the feature frequency noise corresponding to the frequency equal to the product of the number of rotations per second and the number of blades. FIG. 6(B) shows the fan noise spectrum when the cancelling is effected. A three-channel muffler was constructed with respect to the first to third harmonics of the feature frequency noise. This muffler reduces the first to third harmonics of the feature frequency by 30, 20 and 10 Db, respectively.

While in the fourth embodiment (FIG. 4) the band-pass filters and the phase control circuits are dispensed with by utilizing the frequency characteristics of the operational amplifiers, it is possible to dispense with at least one phrase control circuit by changing the positions of installation of the magnetic members 12A (or by appropriately selecting the phase relation between the fan 1 and the rotating disc 2A in the embodiment shown in FIG. 1).

Figure 7:
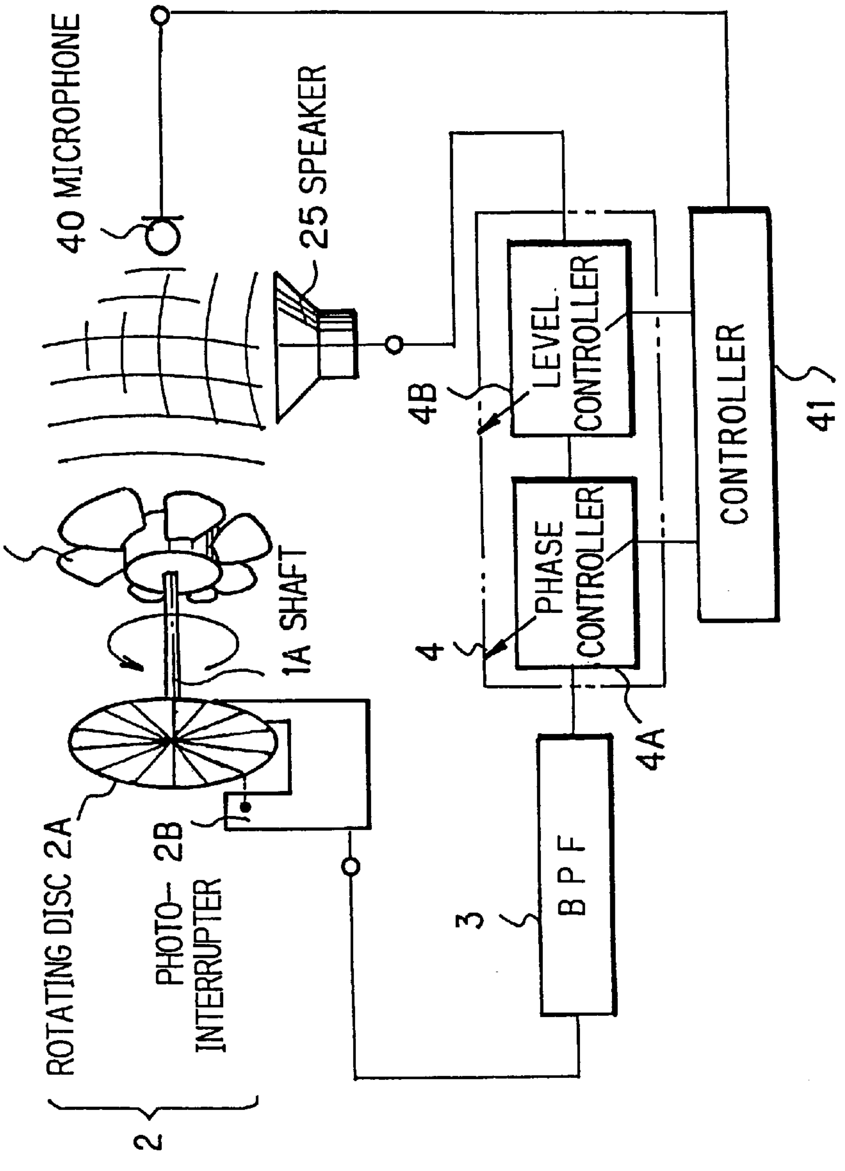
FIG. 7 shows a fifth embodiment of the present invention.
Figure 8:
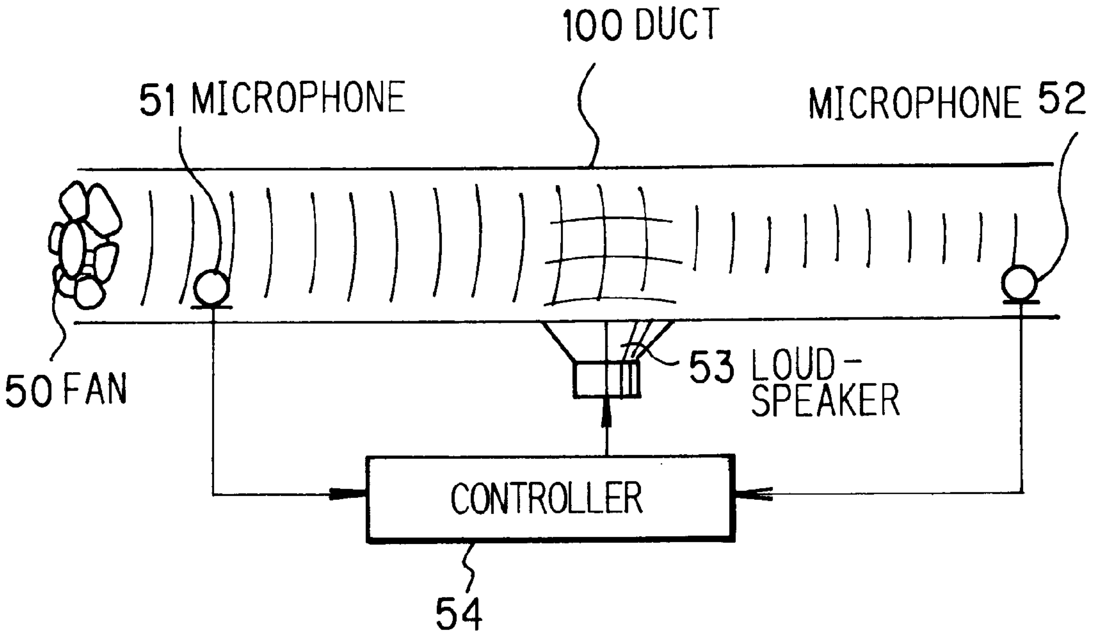
FIG. 8 shows a prior art active system fan noise canceller.

FIG. 7 shows a fifth embodiment of the present invention. Elements similar to those in the embodiment shown in FIG. 1 are designated by like reference numerals and symbols.

This fifth embodiment comprises a noise detecting microphone 40, which is disposed in the fan noise propagation space in the first embodiment shown in FIG. 1 as the noise level detecting means for monitoring the fan noise cancelling status (i.e., the result of interference of the interference sound from the loud-speaker 5). Together with the noise detecting microphone 40, this embodiment comprises a controller 41, which controls the amplitude and phase of the fan noise by controlling the output control means 4 (i.e., the phase controller 4A and level controller 4B) according to the noise level detected by the noise detecting microphone 40, thereby setting an optimum cancelling state. Other elements are the same as in the first embodiment shown in FIG. 1.

The amplitude and phase of the feature frequency component of the fan noise generally change with time or the temperature of the fan noise propagation space. In this embodiment, to cope with these changes the noise detecting microphone 40 monitors the noise present in the fan noise propagation space as a result of the sound wave interference. When the accuracy of the sound wave interference deteriorates, the amplitude and phase of the reference signals are immediately controlled again. The fifth embodiment shown in FIG. 5 seeks to realize optimum sound wave interference by the operation as described above in addition to providing the same functions and effects as in the first embodiment shown in FIG. 1.

As the rotation information detecting means 2, the optical means as shown in FIG. 1 or the magnetic means as shown in FIG. 2 can be utilized. As a further alternative, the shaft of the fan 11 may be divided circumferentially with a conductor into divisions corresponding in number to the number of blades for constructing on-off circuits and detecting sync signals with contacts or by other means.

As has been described in the foregoing, according to the present invention reference signals are obtained directly from the rotational speed of the fan. It is thus possible to eliminate the possibility of howling, extremely reduce the waveform processing time and effectively reduce the noise level of at least the blade passing frequency noise at a high level. It is further possible to dispose opposite waveform sound wave generating means in the vicinity of the source of noise, thus permitting system size reduction and provision of a fan noise canceller, which sufficiently follows variations of the fan rotation and is highly reliable.

Changes in construction will occur to those skilled in the art and various modifications and embodiments may be made without departing from the scope of the present invention. The matter set forth in the foregoing description and accompanying drawings is offered by way of illustration only. It is therefore intended that the foregoing description be regarded as illustrative rather than limiting.

What is claimed is:

1. A fan noise canceller comprising rotation information detecting means for detecting fan rotation information containing the blade passing frequency of noise generated from a fan with the rotation thereof and converting the detected information into an electric signal, a frequency component extracting means for receiving the output of the rotation information detecting means and extracting the blade passing frequency of the noise generated from the fan, an output control means for controlling the amplitude and phase of a blade passing frequency signal of the noise extracted by the frequency component extracting means, and a cancelling loud-speaker for converting an electric signal obtained from the blade passing frequency signal outputted from the output control means into a sound signal for propagation in an interfering relation to noise from the fan, wherein the rotation information detecting means includes a rotatable disc coupled to the shaft of the fan and carrying change information corresponding to the number of blades of the fan, and a signal detector for detecting rotation information of the rotatable disc and outputting signals of the blade passing frequency contained in the rotation information and equal to the product of the number of rotations of the fan and the number of blades thereof and harmonics of the blade passing frequency as electric signals.

2. A fan noise canceller comprising rotation information detecting means for detecting fan rotation information containing the blade passing frequency of noise generated from a fan with the rotation thereof and converting the detected information into an electric signal, a frequency component extracting means for receiving the output of the rotation information detecting means and extracting the blade passing frequency of the noise generated from the fan, an output control means for controlling the amplitude and phase of a blade passing frequency signal of the noise extracted by the frequency component extracting means, and a cancelling loud-speaker for converting an electric signal obtained from the blade passing frequency signal outputted from the output control means into a sound signal for propagation in an interfering relation to noise from the fan, wherein the rotation information detecting means including magnetic members each respectively disposed on each of the fan blades, a magnetic sensor disposed in the vicinity of the fan so as to be capable of facing the magnetic members, and a pre-amplifier for amplifying the output of the magnetic sensor and outputting the amplified output to the frequency component extracting means.

3. A fan noise canceller according to claims 1 or 2, which further comprises a noise level detecting means disposed in a fan noise propagation space for monitoring the fan noise cancelling status, and a controller for controlling the amplitude and phase of frequencies concerning the fan noise by controlling at least the output control means according to the noise level detected by the noise level detecting means, thereby setting an optimum cancelling state.

4. A fan noise canceller comprising:

a rotation information detecting means for detecting noise information of a fan;

a band-pass filter for extracting the blade passing frequency signal from the noise information;

an output control means for controlling the amplitude and phase of the blade passing frequency signal of the extracted noise information; and a cancelling loud-speaker for converting the output of the output control means into a sound signal;

wherein the rotation information detecting means includes a rotatable disc coupled to a shaft of the fan and carrying change information corresponding to the number of fan blades, and a photo-interrupter for outputting signals of the blade passing frequency and harmonics thereof contained in the rotation information of the rotatable disc as electric signals.

5. The fan noise canceller according to any one of claims 1, 2 or 4, wherein the output control means includes a phase controller for setting the opposite phase to the phase of the electric signal obtained from the blade passing frequency signal, and a level controller for setting a level which is of the opposite polarity with respect to the level of the electric signal obtained from the blade passing frequency signal.

* * * * *